United States Patent [19]

Huntress et al.

[11] Patent Number: 4,962,221
[45] Date of Patent: Oct. 9, 1990

[54] CHLORIDE REDUCTION IN POLYSILOXANES

[75] Inventors: Arnold R. Huntress; Daryl D. Landis, both of Midland; Donald E. McVannel, Hemlock, all of Mich.; Timothy Allen, Evansville, Ind.

[73] Assignee: Dow Corning Corporation, Midland, Mich.

[21] Appl. No.: 492,014

[22] Filed: Mar. 12, 1990

[51] Int. Cl.$^5$ .............................................. C07F 7/20
[52] U.S. Cl. .................................. 556/456; 556/450; 556/459; 556/460; 556/461; 556/466; 556/453
[58] Field of Search ............... 556/450, 466, 459, 456, 556/460, 461

[56] References Cited

U.S. PATENT DOCUMENTS 4,127,598 11/1978 McEutee .............................. 556/450
4,156,689 5/1979 Ashby et al. .................... 556/466 X
4,661,612 4/1987 George et al. ...................... 556/450

*Primary Examiner*—Paul F. Shaver
*Attorney, Agent, or Firm*—William F. Boley

[57] ABSTRACT

The instant invention is a process for reducing residual chloride content of polysiloxane fluids, without detrimental effects on the polysiloxane polymer. The process comprises contacting the polysiloxane fluid, containing residual chloride, with selected weakly-basic alkaline metal compounds at a temperature less than 100° C. After an appropriate contact time, the polysiloxane fluid is separated from the solid alkaline metal compounds. In a preferred embodiment of the present invention, water is added to the process to facilitate removal of residual chloride.

15 Claims, No Drawings

CHLORIDE REDUCTION IN POLYSILOXANES

BACKGROUND OF INVENTION

The present invention is a process for removing residual chloride from polysiloxane fluids. The process involves contacting a weakly-basic alkaline metal compound with a chloride containing polysiloxane fluid at a temperature of 100° C. or less. In a preferred embodiment of the present invention, water is added along with the alkaline metal compound to facilitate removal of residual chloride. The treated polysiloxane fluid, reduced in residual chloride content, is filtered to remove solid alkaline metal compounds.

Residual chloride may occur in polysiloxane fluids in a variety of forms. For example the chloride may be present as ionic chloride, as an alkyl chloride, or as chloride bound to silicon. Sources of chloride may be the feed-stocks used to prepare the polysiloxanes, equipment contamination, and added chlorosilanes. The presence of chloride in polysiloxane fluids has been shown to be correlated with such detrimental processes as color changes, viscosity changes, and increased electrical conductivity. To avoid these detrimental processes it is often desirable to reduce residual chloride content of polysiloxanes. The reduction of residual chloride must be achieved without detrimental effect on the polysiloxane.

Welch et al., U.S. Pat. No. 3,278,266, issued Oct. 11, 1966, describes a process for the separation of hydrogen halides from hydrocarbon mixtures. Welch et al. teaches the use of a diacid base, for example magnesium, calcium, strontium, and barium in the form of their respective oxides or hydroxides. The diacid base is deposited on a porous support. The process is run by contacting at temperature above 100° C. and less than 300° C. a vaporized hydrogen mixture with the diacid base.

Williams et al., U.S. Pat. No. 4,721,824, issued Jan. 26, 1988, describes a process whereby extruded particles of magnesium oxide are used to remove chlorides from toluene feedstocks. The particles of magnesium oxide are mixed with an inert binder prior to extrusion. Removal of the organic chlorides was reported to take place at a temperature within the range of 177° C. to about 454° C.

Morehead et al., U.S. Pat. No. 4,732,996, issued March 22, 1988, described a process in which an alkoxysilane is contacted with an alkaline metal compound using superatmospheric pressure to achieve a treatment temperature of greater than 130° C. It is taught that this process will remove ionic chloride species such as free hydrogen chloride and unreacted chlorosilanes as well as non-ionic species including organic chloride materials.

None of the cited reference teach that, at a temperature of 100° C. or less, selected weakly-basic alkaline metal compounds can be used to reduce residual chloride in a polysiloxane fluid without detrimental effects on the polysiloxane polymer. Furthermore, none of the cited reference teach that the reduction of residual chloride in polysiloxane fluid can be facilitated by the addition of water to the process.

SUMMARY OF INVENTION

The present invention is a process for reducing residual chloride content of polysiloxane fluids without detrimental effects on the polysiloxane polymer. The polysiloxane fluid containing residual chloride is contacted with selected weakly-basic alkaline metal compounds at a temperature less than 100° C. After an appropriate contact time, the polysiloxane fluid is separated from the solid alkaline metal compounds. In a preferred embodiment of the present invention, water is added to the process to facilitate removal of residual chloride.

DESCRIPTION OF INVENTION

The present invention is a process for reducing residual chloride content of a polysiloxane fluid. The process comprises contacting the polysiloxane fluid with an alkaline metal compound selected from a group consisting of magnesium oxide, magnesium hydroxide, calcium oxide, calcium hydroxide, barium oxide, and barium hydroxide. The process is conducted at a temperature of 0° C. to 100° C. In a preferred embodiment of the instant invention, a stoichiometric excess of water in relation to hydrolyzable chloride is added to the process.

The polysiloxane fluid consists primarily of organosubstituted polysiloxanes of varying degrees of polymerization (dp). The only requirement regarding the dp, for the instant process, is that the viscosity of the fluid be such that the alkaline metal compound can be mixed with the polysiloxane fluid adequate to insure good contact. In general, the process of the present invention is effective for fluids with a viscosity less than 10,000 centipoise. Higher viscosity fluids may be employed, but mixing and separation of the alkaline metal compounds may be difficult.

The polysiloxanes can be totally methylated fluids, methyl and phenyl substituted fluids, or either type fluid further substituted with minor components of pendant hydroxyl or vinyl groups on silicon atoms. By minor component, is meant less than about 10 mole percent of the pendant group. The polysiloxanes can be either linear or cyclic in structure. The polysiloxanes can be dimethyl and methylphenyl substituted copolymers.

The polysiloxanes can be, for example, trimethylsilyl end-blocked methyl and phenyl substituted polysiloxanes, trimethylsilyl end-blocked dimethylpolysiloxanes, dimethylhydroxylsilyl end-blocked methyl and phenyl substituted polysiloxanes, vinyldimethylsilyl end-blocked dimethylpolysiloxanes, vinyldimethylsilyl end-blocked vinyl and methyl substituted polysiloxanes, trimethylsilyl end-blocked vinyl and methyl substituted polysiloxanes, trimethylsilyl end-blocked methyl and hydroxyl substituted polysiloxanes, methylphenylhydroxysilyl end-blocked methyl and phenyl substituted polysiloxanes dimethylcyclopolysiloxanes, and methyl and phenyl substituted cyclopolysiloxanes.

The term "residual chloride content," as used in the present invention refers to the total chloride present in the polysiloxane fluid. This may include both ionic and non-ionic chloride species. Ionic chloride species include, for example, free hydrogen chloride and chloride substituted on silicon atoms. The non-ionic species include reactive organic chloride materials.

The weakly-basic alkaline metal compound is selected from a group consisting of magnesium oxide, magnesium hydroxide, calcium oxide, calcium hydroxide, barium oxide, and barium hydroxide. Magnesium oxide is the preferred alkaline metal compound. It is important that the alkaline metal compound be a weak base in solution, since strongly basic compounds can cause depolymerization of the polysiloxanes or if the polysiloxanes contain silanol groups, condensation may be catalyzed resulting in molecular weight and viscosity changes.

Particle size of the alkaline metal compound is important to insure adequate contact with the residual chloride within the polysiloxane fluid. In general, a particle size with an average diameter less than two micron is preferred. Larger particle sizes up to about 120 mesh can be used, but effectiveness for removing residual chloride content may be reduced. The lower limit for particle size is limited only by the ability to separate alkaline metal compound from the polysiloxane fluid.

Polysiloxane fluid is typically contacted with an amount of alkaline metal compound sufficient to reduce the chloride content of the fluid to the desired level. The alkaline metal compound is contacted with the polysiloxane fluid within a range of 0.02 to 10.0 weight percent of the combined weight of the two. A preferred weight range is 0.02 to 2 weight percent. Most preferred, is when the alkaline metal compound is contacted with the polysiloxane at about two to five times the stoichiometric equivalence of the residual chloride content.

During contact of the alkaline metal compound with the polysiloxane fluid, the temperature of the contact mixture should be maintained within a range from about 0° C. to 100° C. when water is present in the process. In the absence of water, the upper temperature limit of the process is limited only by the temperature stability of the polysiloxanes. A preferred temperature range, with or without water, is 20° C. to 75° C. Contact time of the alkaline metal compound with the polysiloxane fluid should be within the range of 10 minutes to four hours. Contact times longer than four hours may be employed, but no significant benefit is perceived. A preferred contact time for the alkaline metal compound with the polysiloxane is 0.5 to two hours. Most preferred is about 0.5 to one hour.

The inventors have found that the presence of water during the contact of polysiloxane and alkali metal compound facilitates the removal of residual chloride from the polysiloxane fluid. The inventors believe that this facilitating of the process occurs by the following representative chemical reactions:

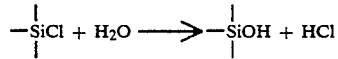
(1)

(2)

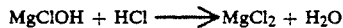
(3)

Of importance to the present invention, is the finding that water facilitates the removal of residual chloride under conditions that do not cause depolymerization or condensation of the polysiloxane polymers and do not cause reaction of pendant groups such as hydroxyl and vinyl when they are present on the polysiloxane. The water can be added to the polysiloxane fluid at the same time it is contacted with the alkaline metal compound. Any amount of water can be beneficial to the process. However, in practice, the preferred amount of water for use in the process is an amount in slight stoichiometric excess of the hydrolyzable chloride content of the polysiloxane fluid and less than the molar equivalent of the alkaline metal compound present in the process. Under these conditions, excess water is bound by the alkaline metal compound and no separate step is required to remove water from the polysiloxane fluid. Greater amounts of water may be used, but to no perceived advantage. By "slight stoichiometric excess" is meant, about a 10 mole percent stoichiometric excess of water in relation to hydrolyzable chloride in the polysiloxane fluid.

When water is used in the process, all other process conditions, with the exception of temperature as previously described, are as previously described for the process without water.

The preferred procedure for conducting the instant described process is in a batch mode, as described above. The equipment and procedures utilized are those known in the art of design and operation of such batch equipment.

The process can also be run in a continuous mode. When the process is run in a continuous mode a large excess of the alkaline metal compound is placed in a vessel such as a tank, column, or the like, known in the art of design of continuous reactors. The system is brought to and maintained at the desired contact temperature by preheating the polysiloxane fluid, heating the vessel in which the alkaline metal compound is contained, or a combination of both. Means for preheating or heating can be effected by conventional means known in the art. Temperature and contact times are as previously described for the batch mode of operation. If the process is to be run with added water, the water is added to the polysiloxane fluid in amounts described for the batch process.

After contact of the polysiloxane fluid with the alkaline metal compound, the polysiloxane fluid is separated from the residual solids, unreacted alkaline metal compound, and salts of reaction of the alkaline metal compound. Separating solids from the treated polysiloxane fluid can be effected by filtration means. Filtration means can be such means as filter presses, bag filters, and cartridge filters.

So that those skilled in the art can better appreciate and understand the present invention, the following examples are given. These examples are presented to be illustrative and are not to be construed as limiting the instant invention as described herein.

Example 1. The ability of magnesium oxide, MgO, to reduce chloride content of a methylphenylhydroxysilyl end-blocked methyl and phenyl substituted polysiloxane fluid was evaluated using a three variable, 15 run, Box-Behnken designed experiment.

The tested polysiloxane had an average chloride content of 241 ppb (parts per billion) and an average Si—OH level of 5.85 wt % (as—OH) of total weight of tested fluid. Each test consisted of heating the polysiloxane fluid to the desired temperature between 35° C. and 70° C.; adding 1.0 wt % Super Cel filter aid, Manville Speciality Chemicals Group, Denver, CO.; adding 0.1 to 1.0 wt % MgO, calcined magnesium oxide, Fisher Scientific, Pittsburg, Pa.; and holding at the desired temperature for the specified time, and then filtering. Reduction in chloride levels was determined by Ion Exchange Chromatography (IEC). The Si—OH levels were determined by Fourier transform infrared analysis. The results are presented in Table 1.

TABLE 1

| Time (min.) | MgO (wt %) | Temp. (°C.) | Cl (ppb) | Si-OH (wt %) |
|---|---|---|---|---|
| 35 | 0.5 | 50 | 73 | 5.83 |
| 35 | 1.0 | 37 | 40 | 5.80 |
| 35 | 1.0 | 70 | 22 | 5.24 |
| 65 | 0.1 | 50 | 201 | 5.63 |
| 65 | 0.5 | 70 | 104 | 5.54 |
| 5 | 0.5 | 40 | 113 | 5.29 |
| 35 | 0.1 | 36 | 164 | 5.81 |
| 35 | 0.5 | 50 | 87 | 5.65 |
| 5 | 0.1 | 50 | 187 | 5.90 |
| 5 | 1.0 | 54 | 58 | 5.80 |
| 35 | 0.1 | 70 | 198 | 5.26 |
| 65 | 0.5 | 36 | 112 | 5.96 |
| 65 | 1.0 | 50 | 73 | 5.50 |
| 5 | 0.5 | 70 | 121 | 6.07 |
| 35 | 0.5 | 50 | 109 | 5.86 |

Statistical analysis indicated that with respect to chloride reduction and Si—OH stability, the optimal conditions were 1.0 wt % MgO, 55°–60° C. contact temperature, and 30–35 minute contact time.

Example 2. The ability of magnesium oxide to reduce residual chloride content of a trimethylsilyl end-blocked methyl and phenyl substituted polysiloxane fluid was evaluated. The polysiloxane fluid was known to contain trimethylchlorosilane as one source of residual chloride. The equilibrated fluid (16,000 lb) was cooled to a temperature below 100° C. and 0.4 lb of water and 1.0 lb of magnesium oxide was added to the fluid. The fluid, water, and MgO were contacted for approximately one hour with constant stirring. At the end of the contact period the fluid was filtered to remove precipitated metal salts. The MgO used was MAGOX 98 HR Fine, C-E Refractories, Valley Forge, Pa., with surface area of 38 to 62 square meters per gram and average particle size less than two microns. Chloride content of the treated polysiloxane fluid was determined by IEC.

The mean chloride content for six untreated polysiloxane samples was 1506 ppb. The mean chloride content for six polysiloxane samples, contacted with MgO for 5–10 minutes prior to filtration, was 449 ppb. When the contact time was increased to one hour, the mean chloride content of the polysiloxane was 73 ppb. The data demonstrate the ability of MgO to reduce chloride content of trimethylsilyl end-blocked methyl and phenyl substituted polysiloxanes and the importance of adequate contact time.

What is claimed is:

1. A process for reducing residual chloride content of a polysiloxane fluid, the process comprising:
    contacting the polysiloxane fluid with an alkaline metal compound selected from a group consisting of magnesium oxide, magnesium hydroxide, calcium oxide, calcium hydroxide, barium oxide, and barium hydroxide; the contact occurring at a contact temperature of 0° C. to 100° C.

2. A process according to claim 1, where an amount of water in slight stoichiometric excess of hydrolyzable chloride content of the polysiloxane fluid and less than molar equivalent of the alkaline metal compound is present.

3. A process according to claim 2, where the contact temperature is 20° C. to 75° C.

4. A process according to claim 3, where the alkaline metal compound has an average particle size less than two microns in diameter.

5. A process according to claim 4, where the polysiloxane fluid is trimethylsilyl end-blocked methyl and phenyl substituted polysiloxanes.

6. The process according to claim 4, where the polysiloxane fluid is methylphenylhydroxysilyl end-blocked methyl and phenyl substituted polysiloxanes.

7. A process according to claim 4, where the polysiloxane fluid is trimethylsilyl end-blocked dimethylpolysiloxanes.

8. A process according to claim 2, where the polysiloxane fluid and the alkaline metal compound are contacted for 0.5 to two hours.

9. A process according to claim 1, where the alkaline metal compound has an average particle size less than two micron in diameter.

10. A process according to claim 1, where the contact temperature is 20° C. to 75° C.

11. A process according to claim 1, where the polysiloxane fluid and the alkaline metal compound are contacted for 0.5 to two hours.

12. A process according to claim 1, where the alkaline metal compound is magnesium oxide.

13. A process according to claim 2, where the polysiloxane fluid is trimethylsilyl end-blocked methyl and phenyl substituted polysiloxanes; the alkaline metal compound is magnesium oxide with a average particle diameter less than two microns; the contact temperature is 20° C. to 75° C.; and the alkaline metal compound and the polysiloxane fluid are contacted for 0.5 to two hours.

14. A process according to claim 2, where the polysiloxane fluid is methylphenylhydroxysilyl end-blocked methyl and phenyl substituted polysiloxanes; the alkaline metal compound is magnesium oxide with an average particle diameter less than two microns; the contact temperature is 20° C. to 75° C.; and the alkaline metal compound and the polysiloxane fluid are contacted for 0.5 to two hours.

15. A process according to claim 2, where the polysiloxane fluid is methyl and phenyl substituted cyclopolysiloxanes; the alkaline metal compound is magnesium oxide with an average particle diameter less than two microns; the contact temperature is 20° C. to 75° C.; and the alkaline metal compound and the polysiloxane fluid are contacted for 0.5 to two hours.

* * * * *